(12) United States Patent
Ren et al.

(10) Patent No.: US 8,222,041 B2
(45) Date of Patent: Jul. 17, 2012

(54) OXYGEN AND CARBON DIOXIDE SENSING

(75) Inventors: Fan Ren, Gainesville, FL (US); Stephen John Pearton, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 0 days.

(21) Appl. No.: 12/990,377

(22) PCT Filed: May 8, 2009

(86) PCT No.: PCT/US2009/043296
§ 371 (c)(1),
(2), (4) Date: Nov. 11, 2010

(87) PCT Pub. No.: WO2009/137768
PCT Pub. Date: Nov. 12, 2009

(65) Prior Publication Data
US 2011/0045600 A1     Feb. 24, 2011

Related U.S. Application Data

(60) Provisional application No. 61/082,010, filed on Jul. 18, 2008, provisional application No. 61/052,047, filed on May 9, 2008.

(51) Int. Cl.
*G01N 33/497* (2006.01)
*G01N 27/00* (2006.01)

(52) U.S. Cl. .......... 436/133; 422/82.01; 422/82.02; 422/82.03; 422/82.04; 422/83; 422/84; 422/88; 422/90; 422/98; 436/68; 436/127; 436/136; 436/151

(58) Field of Classification Search .... 422/82.01–82.04, 422/83–84, 88, 90, 98; 436/68, 127, 133, 436/136, 151
See application file for complete search history.

(56) References Cited

U.S. PATENT DOCUMENTS

| 4,777,019 | A | * | 10/1988 | Dandekar | 422/82.02 |
| 5,001,531 | A | * | 3/1991 | Yamaguchi et al. | 257/414 |
| 6,433,356 | B1 | * | 8/2002 | Cahen et al. | 257/40 |
| 7,053,425 | B2 | | 5/2006 | Sandvik et al. | |
| 7,361,946 | B2 | * | 4/2008 | Johnson et al. | 257/253 |
| 2003/0017683 | A1 | * | 1/2003 | Emrick et al. | 438/478 |
| 2003/0134427 | A1 | | 7/2003 | Roller et al. | |
| 2005/0129573 | A1 | | 6/2005 | Gabriel et al. | |

(Continued)

FOREIGN PATENT DOCUMENTS

DE    10032062 C2    1/2002

(Continued)

OTHER PUBLICATIONS

Zhou, R. et al, Sensors and Actuatos B 1996, 33, 188-193.*

(Continued)

*Primary Examiner* — Arlen Soderquist
(74) *Attorney, Agent, or Firm* — Saliwanchik, Lloyd & Eisenschenk

(57) ABSTRACT

A high electron mobility transistor (HEMT) capable of performing as a $CO_2$ or $O_2$ sensor is disclosed, hi one implementation, a polymer solar cell can be connected to the HEMT for use in an infrared detection system. In a second implementation, a selective recognition layer can be provided on a gate region of the HEMT. For carbon dioxide sensing, the selective recognition layer can be, in one example, PEI/starch. For oxygen sensing, the selective recognition layer can be, in one example, indium zinc oxide (IZO). In one application, the HEMTs can be used for the detection of carbon dioxide and oxygen in exhaled breath or blood.

23 Claims, 9 Drawing Sheets

U.S. PATENT DOCUMENTS

| | | | |
|---|---|---|---|
| 2005/0245836 A1* | 11/2005 | Star et al. | 600/532 |
| 2005/0247961 A1* | 11/2005 | Zhou | 257/213 |
| 2005/0263790 A1 | 12/2005 | Moon et al. | |
| 2006/0102926 A1* | 5/2006 | Kikkawa et al. | 257/103 |
| 2006/0118903 A1* | 6/2006 | Cahen et al. | 257/494 |
| 2007/0048181 A1 | 3/2007 | Chang et al. | |
| 2007/0164321 A1* | 7/2007 | Sheppard et al. | 257/256 |
| 2007/0224128 A1* | 9/2007 | Dennis et al. | 424/10.1 |
| 2008/0203431 A1* | 8/2008 | Garcia et al. | 257/192 |
| 2008/0302672 A1* | 12/2008 | Sandvik et al. | 205/775 |
| 2010/0007326 A1* | 1/2010 | Nakazato | 324/71.5 |

FOREIGN PATENT DOCUMENTS

| | | | |
|---|---|---|---|
| DE | 10062044 | * | 6/2002 |

OTHER PUBLICATIONS

Chi, L.-L. et al, Materials Chemistry and Physics 2000, 63, 19-23.*
Schalwig, J. et al, Physica Status Solidi (a) 2001, 185, 39-45.*
Wu, D. G. et al, Chemistry—A European Journal 2001, 7 1743-1749.*
Ashkenasy, G. et al, Accounts of Chemical Research 2002, 35, 121-128.*
Schalwig, J. et al, Sensors and Actuators B 2002, 87, 425-430.*
Luo, B. et al, Solid-State Electronics 2003, 47, 1015-1020.*
Shimanoe, K. et al, Sensors and Actuators b 2004, 102, 14-19.*
Chaniotakis, N. A. et al, Analytical Chemistry 2004, 76, 5552-5556.*
Star A. et al, Advanced Materials 2004, 16, 2049-2052.*
Kang, B. S. et al, Physica Status Solidi (c) 2005, 2, 2672-2675.*
Alifragis, Y. et al, Physica Status Solidi (a) 2007, 204, 2059-2063.*
Gassull, D. et al, Journal of Physical Chemistry C 2007, 111, 12414-12419.*
Sberveglieri, G. et al, Sensors and Actuators B 1995, 24-25, 588-590.*
Nomura, K. et al, Science 2003, 300, 1269-1272.*
Hosono, H., International Journal of Applied Ceramic Technology 2004, 1, 106-118.*
Martins, R. et al, Physica Status Solidi A 2005, 202, R95-R97.*
Lee, D.-H. et al, Advanced Materials 2007, 19, 843-847.*
Donghun Kang et al., "Amorphous gallium indium zinc oxide thin film transistors: Sensitive to oxygen molecules," May 7, 2007, Applied Physics Letters 90, 192101.
G. Sonnabend et al., "High-resolution observations of Martian non-thermal $CO_2$ emission near 10μm with a new tuneable heterodyne receiver," Dec. 31, 2005, Astronomy & Astrophysics 435, pp. 1181-1184.
B. S. Kang et al., "Exhaled-Breath Detection Using AIGaN/GaN High Electron Mobility Transistors Integrated with a Peltier Element," Dec. 26, 2007, Electrochemical and Solid-State Letters, vol. 11, Issue 3, pp. J19-J21.
C. Y. Chang et al., "$CO_2$ detection using polyethylenimine/starch functionalized AIGaN/GaN high electron mobility transistors," Jun. 10, 2008, Applied Physics Letters 92, 232102.
Yu-Lin Wang et al., "Oxygen gas sensing at low temperature using indium zinc oxide-gated AIGaN/GaN high electron mobility transistors," Mar. 25, 2010, Journal of Vacuum Science and Technology B, vol. 25, Issue 2, pp. 376-379.

* cited by examiner

OXYGEN AND CARBON DIOXIDE SENSING

CROSS-REFERENCE TO RELATED APPLICATIONS

This application is the U.S. national stage application of International Patent Application No. PCT/US2009/043296, filed May 8, 2009, which claims priority to U.S. Provisional Application Ser. No. 61/052,047, filed May 9, 2008, and U.S. Provisional Application Ser. No. 61/082,010, filed Jul. 18, 2008, the disclosures of each of which are incorporated by reference herein in their entirety, including any figures, tables, or drawings.

GOVERNMENT SUPPORT

This invention was made with government support under Grant No. N000140710982 awarded by the Office of Naval Research (ONR), Grant No. NAG 3-2930 awarded by the Kennedy Space Center National Aeronautics and Space Administration (NASA), and Grant No. 0400416 awarded by the National Science Foundation (NSF) Division of Materials Research (DMR). The government has certain rights in the invention.

BACKGROUND OF INVENTION

The detection of carbon dioxide ($CO_2$) gas has attracted attention in the context of global warming, biological and health-related applications such as indoor air quality control, process control in fermentation, and in the measurement of $CO_2$ concentrations in patients' exhaled breath with lung and stomach diseases.

In medical applications, it can be critical to monitor the $CO_2$ and $O_2$ concentrations in the circulatory systems for patients with lung diseases in the hospital. The current technology for $CO_2$ measurement typically uses IR instruments, which can be very expensive and bulky.

The most common approach for $CO_2$ detection is based on non-dispersive infrared (NDIR) sensors, which are the simplest of the spectroscopic sensors. The best detection limits for the NDIR sensors are currently in the range of 20-10,000 ppm. The key components of the NDIR approach are an infrared (IR) source, a light tube, an interference filter, and an infrared (IR) detector. In operation, gas enters the light tube. Radiation from the IR light source passes through the gas in the light tube to impinge on the IR detector. The interference filter is positioned in the optical path in front of the IR detector such that the IR detector receives the radiation of a wavelength that is strongly absorbed by the gas whose concentration is to be determined while filtering out the unwanted wavelengths. The IR detector produces an electrical signal that represents the intensity of the radiation impinging upon it. It is generally considered that the NDIR technology is limited by power consumption and size.

In recent years, monomers or polymers containing aminogroups, such as tetrakis(hydroxyethyl)ethylenediamine, tetraethylene-pentamine and polyethyleneimine (PEI) have been used for $CO_2$ sensors to overcome the power consumption and size issues found in the NDIR approach. Most of the monomers or polymers are utilized as coatings of surface acoustic wave transducers. The polymers are capable of adsorbing $CO_2$ and facilitating a carbamate reaction. PEI has also been used as a coating on carbon nanotubes for $CO_2$ sensing by measuring the conductivity of nanotubes upon exposing to the $CO_2$ gas. For example, $CO_2$ adsorbed by a PET coated nanotube portion of a NTFET (nanotube field effect transistor) sensor lowers the total pH of the polymer layer and alters the charge transfer to the semiconducting nanotube channel, resulting in the change of NTFET electronic characteristics.

The current technology for $O_2$ measurement, referred to as oximetry, is small and convenient to use. However, the $O_2$ measurement technology does not provide a complete measure of respiratory sufficiency. A patient suffering from hypoventilation (poor gas exchange in the lungs) given 100% oxygen can have excellent blood oxygen levels while still suffering from respiratory acidosis due to excessive $CO_2$. The $O_2$ measurement is also not a complete measure of circulatory sufficiency. If there is insufficient blood flow or insufficient hemoglobin in the blood (anemia), tissues can suffer hypoxia despite high oxygen saturation in the blood that does arrive. The current oxide-based $O_2$ sensors can operate at very high temperatures, such as the commercialized solid electrolyte $ZrO_2$ (700° C.) or the semiconductor metal oxides such as $TiO_2$, $Nb_2O_5$, $SrTiO_3$, and $CeO_2$ (>400° C.). However, it remains important to develop a low operation temperature and high sensitivity $O_2$ sensor to build a small, portable and low cost $O_2$ sensor system for biomedical applications.

BRIEF SUMMARY

Embodiments of the present invention relate to a high electron mobility transistor (HEMT) capable of performing as a $CO_2$ or $O_2$ sensor. In a specific embodiment, the HEMT can be used for the detection of carbon dioxide and oxygen in exhaled breath or blood.

According to one embodiment of the invention, a polymer solar cell can be provided on a gate region of the HEMT. In a specific embodiment, the combination of polymer solar cell and HEMT can be utilized with a light source for an infrared detection system.

According to another embodiment of the invention, a selective recognition layer can be provided on a gate region of the HEMT. In a specific embodiment for carbon dioxide sensing, the selective recognition layer can be PEI/starch. In a specific embodiment for oxygen sensing, the selective recognition layer can be indium zinc oxide (IZO).

In one implementation of the subject sensors, the carbon dioxide sensor and oxygen sensor can be provided in a single chip. The combined sensor device can be used to monitor the $CO_2$ and $O_2$ concentrations in the circulatory systems for patients with lung diseases in the hospital. Other embodiments can be used for fuel cell or environmental applications.

In another implementation of the subject sensors, the carbon dioxide sensor and oxygen sensor can be integrated with other gas sensors, such as hydrogen or carbon monoxide sensors, in a single chip.

Embodiments of the disclosed sensors can be integrated to a wireless transmitter for constant monitoring and reporting.

DETAILED DISCLOSURE

Figure 1:
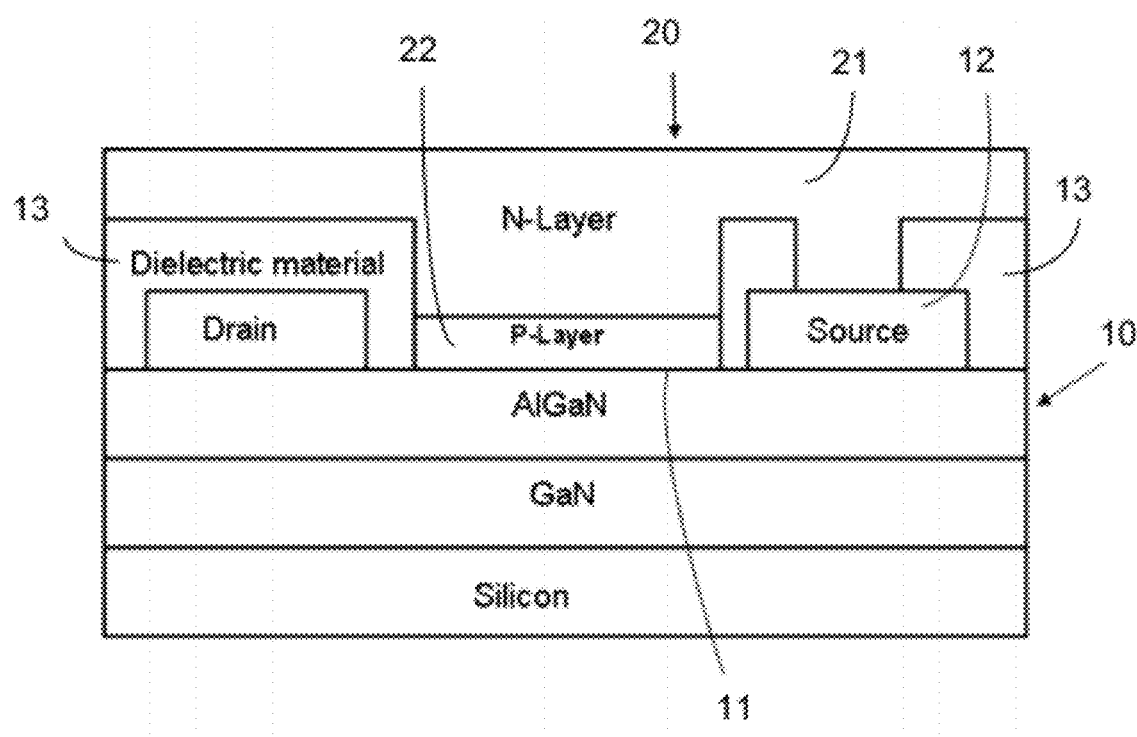
FIG. 1 shows an integrated solar cell and HEMT capable of being used for $CO_2$ and oxygen sensing.

Embodiments of the present invention relate to a high electron mobility transistor (HEMT) capable of performing as a carbon dioxide sensor. Other embodiments of the present invention relate to a HEMT capable of performing as an oxygen sensor. Certain embodiments can be used for the detection and reporting of carbon dioxide and/or oxygen concentration for a patient. In an embodiment of the invention, the subject sensor can be utilized in an infrared (IR) detector for carbon dioxide sensing. Other embodiments of the subject sensor can be utilized in situ to detect and report carbon dioxide and/or oxygen directly. In one embodiment, the sensor can be portable. In another embodiment, the sensor can be implantable.

One embodiment of present invention integrates a polymer-based solar cell with a HEMT. The integrated polymer-based solar cell and HEMT can be used to measure $CO_2$ and oxygen in, for example, an IR detection system.

Another embodiment of the present invention utilizes a functionalized gate area of a HEMT to measure $CO_2$ and oxygen directly (i.e. without a light source).

Embodiments of the present invention can be used for continuous $CO_2$ or $O_2$ monitoring. The subject devices can be portable. In many embodiments, the subject devices can be low cost.

In specific embodiments, the subject devices can be used for medical applications. For example, embodiments of the subject sensors can be used to measure $CO_2$ and oxygen concentration in exhaled breath or blood.

Embodiments of a $CO_2$ and $O_2$ sensing HEMT can be integrated with other sensors, such as pH or blood glucose detection sensors, in a single chip.

HEMTs can operate over a broad range of temperatures and form the basis of next-generation microwave communication systems. Accordingly, embodiments of the present invention can be implemented as an integrated sensor/wireless chip.

Embodiments utilizing the HEMT sensor can provide a fast response time. In a further embodiment, the subject device can be used as a wireless based sensor to send the testing results to a display or separate device. In one embodiment, the sensor can be integrated to the wireless transmitter for constant $CO_2$ and $O_2$ monitoring.

In certain embodiments an AlGaN/GaN HEMT can be used for the HEMT of the subject sensors.

For the embodiments having the integrated polymer-based solar cell and HEMT, IR and far IR can be detected. $CO_2$ and $O_2$ have absorption bands in the visible, IR and far IR ranges, which are not absorbed by the wide energy bandgap AlGaN/GaN material. Once the polymer-based solar cell on the gate area of the AlGaN/GaN HEMT absorbs the light (specific wavelengths for $CO_2$ or $O_2$), the charges created by the solar cell are amplified by the HEMT. The intensity of the light depends on the concentrations of $CO_2$ or $O_2$. Accordingly, embodiments of the subject device can be used to measure $CO_2$ or $O_2$ concentration.

AlGaN/GaN High Electron Mobility Transistors (HEMTs) include a high electron mobility and high electron sheet carrier concentration channel induced by piezoelectric polarization of the strained AlGaN layer. A variety of gas, chemical and health related sensors based on HEMT technology have been demonstrated with proper surface functionalization on the gate area of the HEMTs. For example, hydrogen, mercury ion, prostate specific antigen, DNA, and glucose detection have been accomplished using HEMTs.

Figure 10:
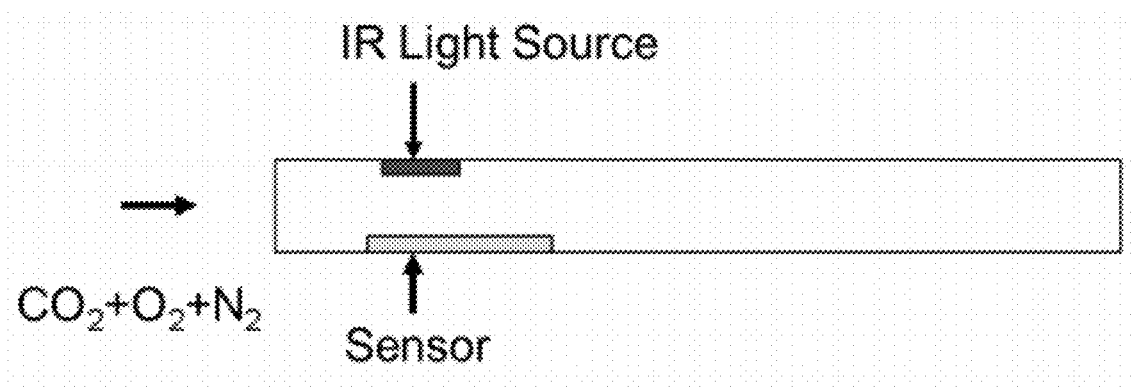
FIG. 10 shows a representation of an infrared detection system according to an embodiment.

However, AlGaN and GaN are wide energy bandgap materials that do not absorb visible light or light with wavelength longer than the visible light. In order to modify an AlGaN/GaN-based HEMT sensor for sensing $CO_2$ and $O_2$ in IR detection schemes, embodiments of the present invention functionalize the AlGaN/GaN HEMT gate region with a polymer-based solar cell, for which the light absorption wavelengths can be tuned by adding nano-particles or nano-rods and dyes in the polymer film. The amount of light reaching the solar cell depends on the concentration of $CO_2$ and $O_2$ in the light path between the solar cell and light source. The charges in the solar cell can be amplified by the HEMT, which correspond to the concentration of $CO_2$ and $O_2$. In certain embodiments, a light source, such as a light bulb, LED, or laser can be used to provide the incident light impinging upon the subject polymer-based solar cell integrated HEMT. FIG. 10 shows an example IR detection system in which a detection scheme is illustrated. The subject polymer-based solar cell integrated HEMT sensor detects the $CO_2$ and/or $O_2$ from the amount of light reaching the sensor.

Referring to FIG. 1, a sensor according to an embodiment of the present invention can include a HEMT 10 with a polymer-based solar cell 20 formed on the gate 11 of the HEMT (having the structure of a field effect transistor). The solar cell 20 can include a P—N junction applied to the gate region 11 of the HEMT. The N-type conductive portion 21 of the solar cell 20 can be grounded to the source 12 of the HEMT 10. This can be accomplished by connecting the N-type conductive portion 21 of the solar cell 20 to the source electrode 12 of the HEMT 10 through a via in the dielectric material 13 covering the source electrode 12. The P-type conductive portion 22 of the solar cell 20 can be disposed on the gate region 11 of the HEMT 10. Although not shown in the figures, in one embodiment, the HEMT can have a bipolar transistor structure and can be connected to the polymer solar cell in an amplifying configuration.

In many embodiments, a polymer based solar cell-gated HEMT can be used as a $CO_2$ and $O_2$ sensor. Although the HEMT for the integrated polymer based solar cell and HEMT has been described as an AlGaN/GaN HEMT, other HEMTs, such as an AlGaAs/GaAs HEMT, an InGaP/GaAs HEMT or an InAlAs/InGaAs HEMT can be used in place of the AlGaN/GaN HEMT.

Other embodiments of the present invention can be used in situ (e.g. not within an IR system) by coating the gate of the HEMT with particular materials for selective recognition. In one embodiment $CO_2$ sensing can be accomplished using a starch-functionalized gated HEMT; and $O_2$ sensing can be accomplished using an oxide.

Embodiments of the present invention provide design and fabrication of chemically functionalized HEMT device for $CO_2$ sensing. Specific sensitivity can be achieved by employing a $CO_2$ recognition layer on the gate area of the HEMT. In a preferred embodiment the $CO_2$ recognition layer comprises PEI/starch. Other polymers containing amino group also can be used. For example, aminopropyldimethylsiloxane (APDMS), polystyrene ethylene diamine (PSEDA), propylaminopropylpolysiloxane (PAPPS) and polypropylenimine (PPI) can be used as the recognition layer.

Figure 2A:
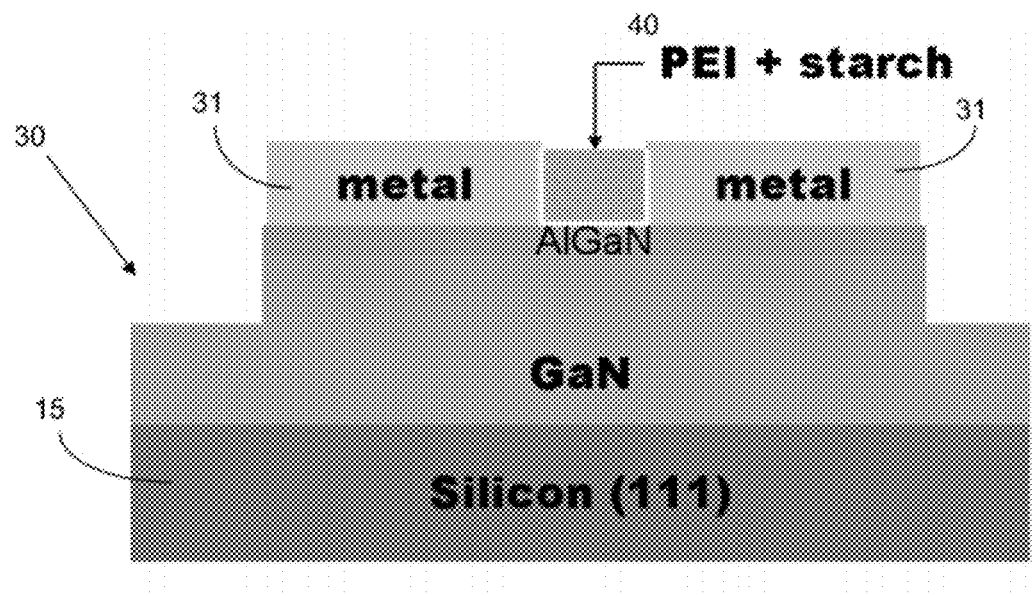
FIG. 2A shows a cross-sectional schematic of an AlGaN/GaN HEMT based $CO_2$ sensor according to an embodiment.
Figure 2B:
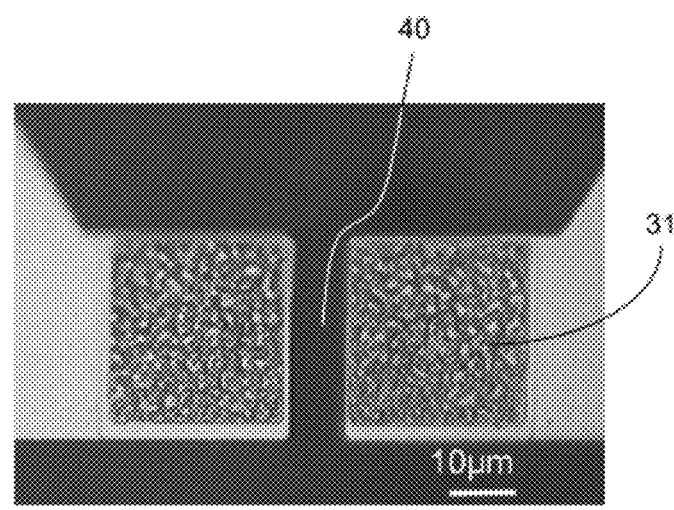
FIG. 2B shows a plan view photomicrograph of a PEI/starch functionalized HEMT $CO_2$ sensor according to an embodiment.

Referring to FIGS. 2A and 2B, an AlGaN/GaN HEMT 30 can be provided with a polymer, such as PEI+starch, 40 on the gate region. The AlGaN/GaN HEMT structure can include an undoped GaN buffer on a substrate. The substrate can be, for example, a silicon substrate 15. An undoped AlGaN spacer can be provided on the GaN buffer, and a Si-doped AlGaN cap layer can be provided on the undoped AlGaN spacer. Ohmic contacts can be provided on the AlGaN cap layer with metal contacts 31 formed thereon. The selective recognition layer 40 can be provided on the gate region between the metal contacts 31. Although not shown in the figure, a passivation layer can be provided on the device to cover the source/drain regions while exposing the gate region.

Although the HEMT for the aforementioned embodiments (and example provided below) has been described as an AlGaN/GaN HEMT, other HEMTs, such as an AlGaAs/GaAs HEMT, an InGaP/GaAs HEMT or an InAlAs/InGaAs HEMT can be used in place of the AlGaN/GaN HEMT.

Embodiments of the present invention provide a high sensitivity and low operation temperature $O_2$ sensor. The oxygen can be sensed by using a selective recognition layer provided on a gate area of an HEMT. The selective recognition layer can be an oxide. In a specific embodiment, the subject sensor is fabricated by employing an indium zinc oxide (IZO) film on a gate area of the HEMT. The highly $O_2$-sensitive IZO film, and the high electron mobility and high carrier concentration of HEMTs can realize the low temperature and high sensitivity $O_2$ sensors. In other embodiments, the selective recognition layer oxide can be, for example, ZnO, InGaZnO, $SnO_2$, or $TiO_2$.

The IZO film can be grown in a high oxygen vacancy concentration.

Figure 6:
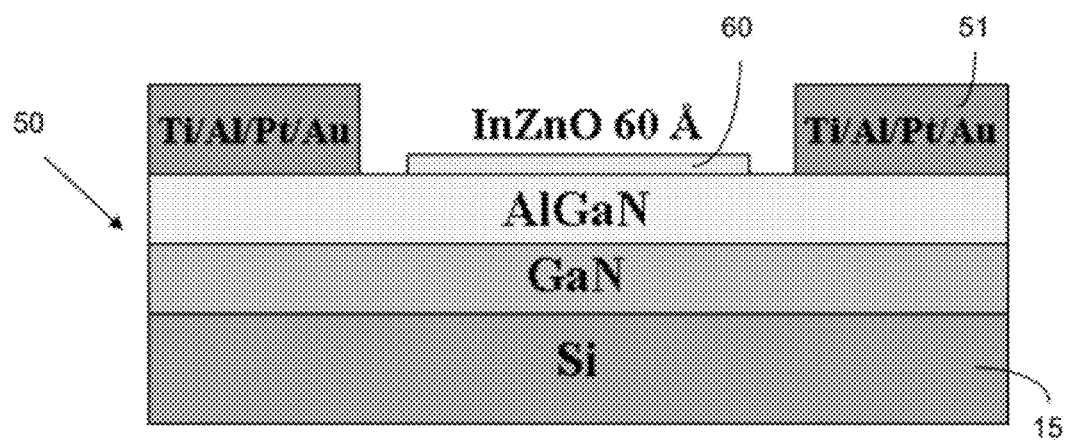
FIG. 6 shows a cross-sectional schematic of an AlGaN/GaN HEMT $O_2$ sensor according to an embodiment.

Referring to FIG. 6, an AlGaN/GaN HEMT 50 can be provided with metal-oxide or semiconductor metal-oxide on the gate region. The AlGaN/GaN HEMT structure can include an undoped GaN buffer on a substrate. The substrate can be, for example, a silicon substrate 15. An undoped AlGaN spacer can be provided on the GaN buffer, and a Si-doped AlGaN cap layer can be provided on the undoped AlGaN spacer. Ohmic contacts can be provided on the AlGaN cap layer with metal contacts 51 formed thereon. A selective recognition layer 60 can be provided on the gate region between the metal contacts 51. In a specific embodiment as shown in FIG. 6, the selective recognition layer 60 can be IZO. Although not shown in the figure, a passivation layer can be provided on the device to cover the source/drain regions while exposing the gate region.

Although the HEMT for the aforementioned embodiments (and example provided below) has been described as an AlGaN/GaN HEMT, other HEMTs, such as an AlGaAs/GaAs HEMT, an InGaP/GaAs HEMT or an InAlAs/InGaAs HEMT can be used in place of the AlGaN/GaN HEMT.

In accordance with the invention, embodiments include, but are not limited to, the following:

1. A carbon dioxide sensor, comprising a high electron mobility transistor (HEMT) comprising a selective recognition layer on a gate region, the selective recognition layer being selective for carbon dioxide.

2. The carbon dioxide sensor according to embodiment 1, wherein the selective recognition layer comprises a polymer containing amino groups. The selective recognition layer can be, for example, PEI/starch, APDMS, PSEDA, PAPPS, or PPI.

3. An oxygen sensor, comprising: a high electron mobility transistor (HEMT) comprising a selective recognition layer on a gate region, wherein the selective recognition layer has a high oxygen vacancy concentration. The selective recognition layer can be, for example, a zinc oxide, indium-zinc-oxide, or indium-gallium-zinc-oxide, or a tin-oxide or titanium-oxide.

4. A sensor, comprising: a high electron mobility transistor (HEMT); and a polymer based solar cell connected to the HEMT.

5. The sensor according to embodiment 4, wherein an N-type region of the polymer based solar cell is connected to a source region of the HEMT.

6. The sensor according to embodiment 4 or 5, wherein the polymer based solar cell can be provided on a gate region of the HEMT.

7. The sensor according to embodiment 4, wherein the sensor is used in an IR detection system to measure $CO_2$ and/or oxygen.

8. A method of detecting oxygen and carbon dioxide in exhaled breath, comprising: providing a sensor device in or near exhaled breath of a patient, wherein the sensor device comprises:
   a first high electron mobility transistor (HEMT) on a substrate and comprising a layer of PEI/starch, APDMS, PSEDA, PAPPS, or PPI on a gate region of the first HEMT; and
   a second HEMT on the substrate and comprising zinc-oxide, indium-zinc-oxide, indium-gallium-zinc-oxide, tin-oxide, or titanium oxide on a gate region of the second HEMT.

9. The method according to embodiment 8, further comprising: recycling the second HEMT by performing an annealing process; and performing a second test of the oxygen and carbon dioxide in the exhaled breath.

10. A method of detecting oxygen and carbon dioxide in exhaled breath, comprising: providing an infrared (IR) detection system in or near a path of exhaled breath of a patient, wherein the IR detection system comprises:
   a polymer based solar cell on a gate region of a HEMT, wherein the polymer based solar cell converts incident light into electric signals and the HEMT amplifies the electrical signals.

11. A method of detecting oxygen and carbon dioxide in exhaled breath, comprising: providing an infrared (IR) detection system in or near a path of exhaled breath of a patient, wherein the IR detection system comprises:
   a high electron mobility transistor (HEMT); and a polymer based solar cell connected to the HEMT, wherein the polymer based solar cell converts incident light into electric signals and the HEMT amplifies the electrical signals.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

EXAMPLE $CO_2$ Recognition Layer-gated Functionalized HEMT

The AlGaN/GaN HEMT structures used for the following examples have a 3 μm thick undoped GaN buffer, a 30 Å thick undoped $Al_{0.3}Ga_{0.7}N$ spacer, and a 220 Å thick Si-doped $Al_{0.3}Ga_{0.7}N$ cap layer. The epi-layers were grown by Metal-Organic Chemical Vapor Deposition (MOCVD) on thick GaN buffers on silicon (111) substrates. Mesa isolation was performed by inductively coupled plasma (ICP) etching with $Cl_2$/Ar discharges at −90V dc self-bias, ICP power of 300 W at 2 MHz and a process pressure of 5 m Torr. Ohmic contacts each having an area of 50×50 μm$^2$ and separated with gap of 10 μm were formed of e-beam deposited Ti (200 Å)/Al (800 Å)/Pt (400 Å)/Au (800 Å) patterned by lift-off. The contacts were annealed at 850° C. for 45 sec under a flowing $N_2$ ambient in a Heatpulse 610T system. The final metal step was deposition of e-beam evaporated Ti (300 Å)/Au (1200 Å) interconnection contacts. A mixture of PEI and starch was used for the $CO_2$ selective recognition layer and the mixture was spin-coated on the gate region of the HEMT. 500-nm-thick polymethyl methacrylate (PMMA) was used to encapsulate the source/drain regions, with only the gate region opened using e-beam lithography. A plan view photomicrograph of a completed device and a schematic cross-section of the device are shown in FIGS. 2A and 2B.

The effect of temperature and $CO_2$ concentration on the sensing sensitivity was investigated using the above described devices. For these examples, the source-drain current-voltage characteristics of the HEMT sensors were measured at various temperatures and $CO_2$ concentrations using Agilent 4145B parameter analyzer.

Accordingly, the completely fabricated device was bonded to an electrical feed-through and exposed to various $CO_2$ concentrations ambient balanced with $N_2$. The gas exposure sequence consisted of repeated exposures to gas with different $CO_2$ concentration balanced with pure $N_2$.

Figure 3:
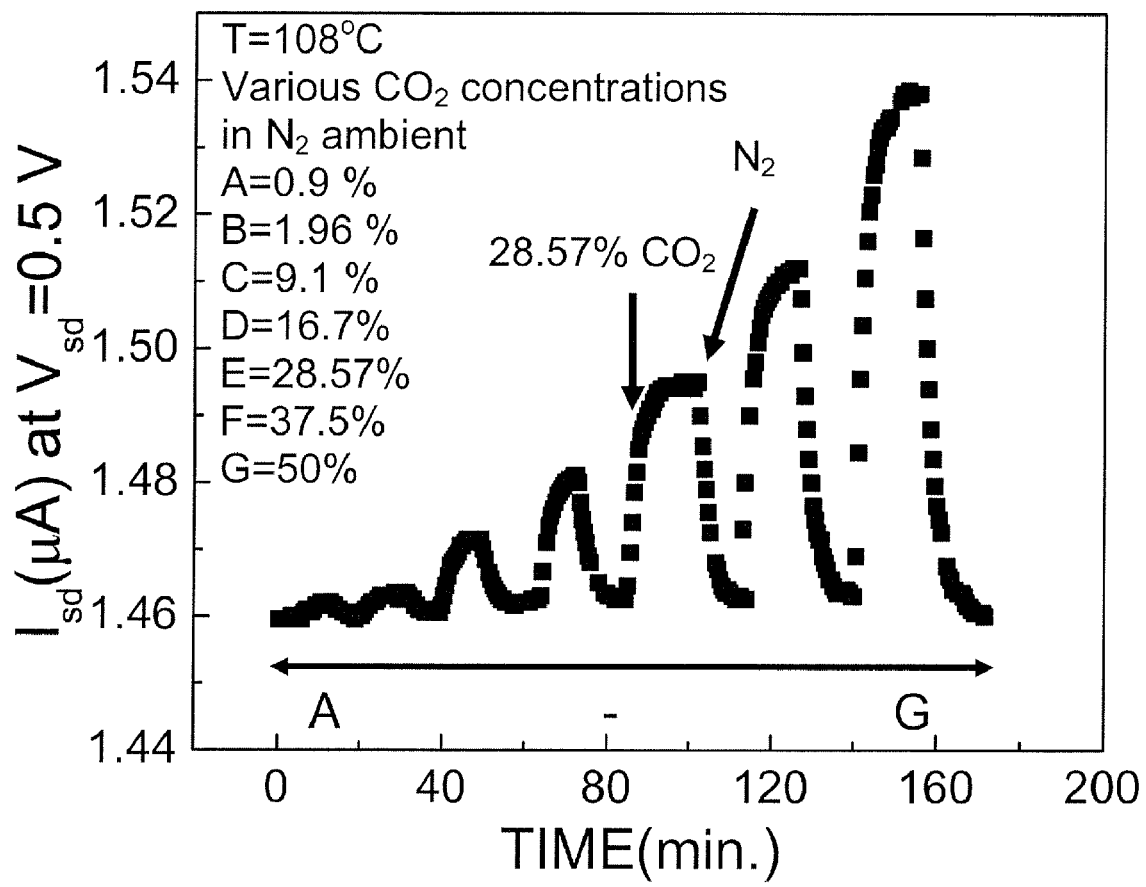
FIG. 3 shows a plot of drain current measured at fixed source-drain during exposure to different $CO_2$ concentration ambients of a PEI/starch functionalized HEMT sensor according to an embodiment. The drain bias voltage was 0.5 V and measurements were conducted at 108° C.

The interaction between $CO_2$ and amino group-containing compounds with the influence of water molecules is based on an acid-base reaction. The purpose of adding starch into the PEI in the experimental embodiment was to enhance the absorption of the water molecules into the PEI/starch thin film. Several possible reaction mechanisms have been suggested. The key reaction was that primary amine groups, —$NH_2$, on the PEI main chain reacted with $CO_2$ and water to form —$NH_3^+$ ions, and the $CO_2$ molecule became $OCOOH^−$ ions. Thus, the charges, or the polarity, on the PEI main chain were changed. The electrons in the two-dimensional electron gas (2DEG) channel of the AlGaN/GaN HEMT are induced by piezoelectric and spontaneous polarization effects. This 2DEG channel is located at the interface between the GaN layer and AlGaN layer. There are positive counter charges at the AlGaN surface layer induced by the 2DEG channel. Any slight changes in the ambient of the AlGaN/GaN HEMT affect the surface charges of the AlGaN/GaN HEMT. The PEI/starch was provided on the gate region of the HEMT. The charges of the PEI changed through the reactions between —$NH_2$ and $CO_2$ as well as water molecules. These are then transduced into a change in the concentration of the 2DEG in the AlGaN/GaN HEMTs. FIG. 3 shows the drain current of PEI/starch functionalized HEMT sensors measured exposed to different $CO_2$ concentration ambients. The measurements were conducted at 108° C. and a fixed source-drain bias voltage of 0.5 V. The current increased with the introduction of $CO_2$ gas. This was due to the net positive charges increased on the gate area, thus inducing electrons in the 2DEG channel. The response to $CO_2$ gas has a wide dynamic range from 0.9% to 50%. Higher $CO_2$ concentrations were not tested. The response times were on the order of 100 seconds. The signal decay time was slower than the rise time because of the longer time required to purge $CO_2$ out from the test chamber.

Figure 4:
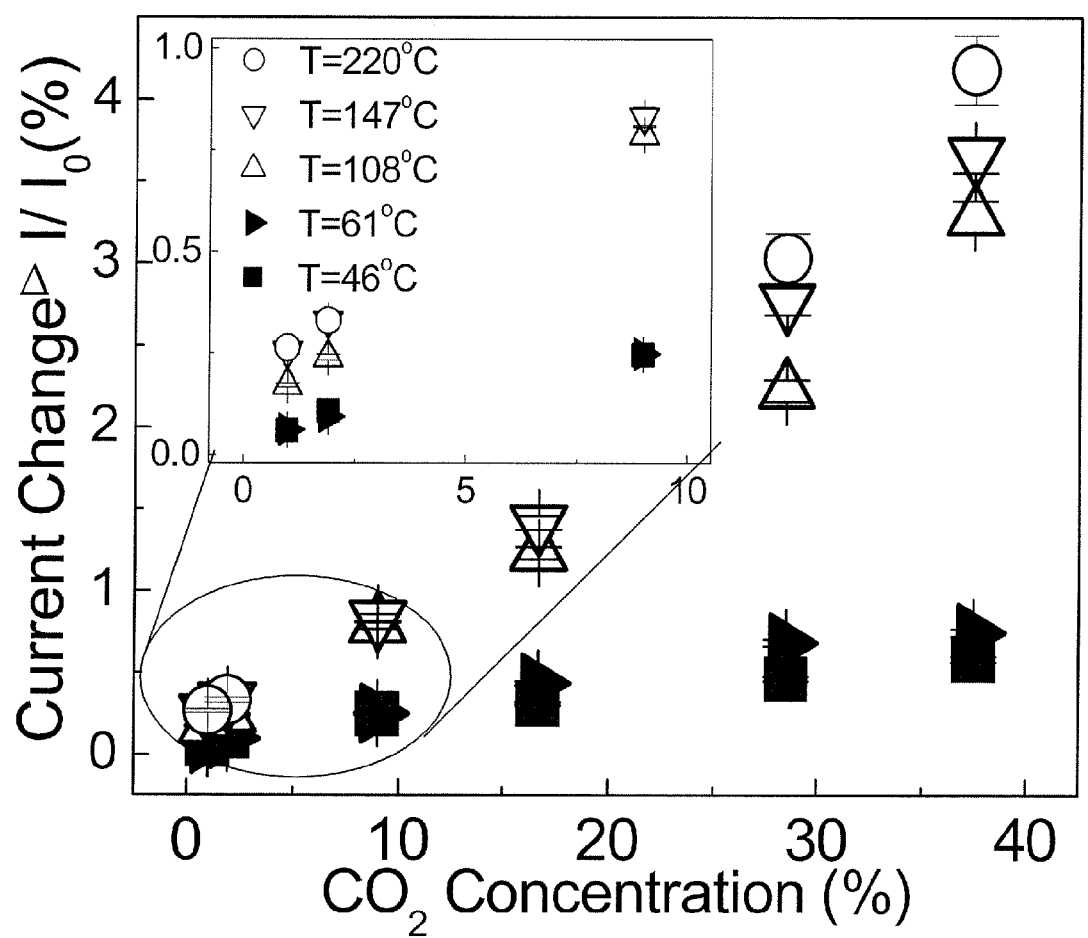
FIG. 4 shows a plot of the drain current changes of an embodiment of the subject HEMT sensor as a function of $CO_2$ concentration. The inset is the current change of the sensors as function of lower $CO_2$ concentrations (0.9-10%).
Figure 5:
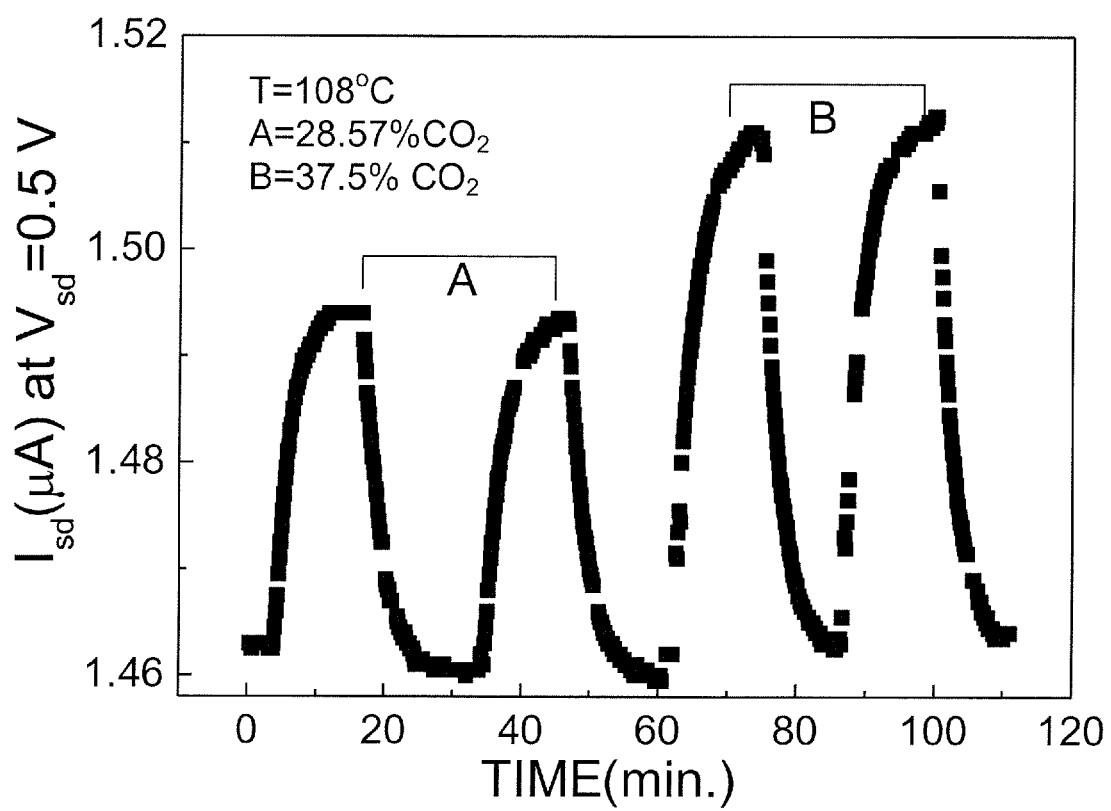
FIG. 5 shows a plot of the drain current of a PEI/starch functionalized HEMT sensor as a function of time measured at a drain bias voltage of 0.5 V and at 108° C.

The effect of ambient temperature on $CO_2$ detection sensitivity was investigated. FIG. 4 shows the percentage of drain current change as a function of $CO_2$ concentration from 0.9% to 40% at five different testing temperatures ranging from 46° C. to 220° C. The insert of FIG. 4 shows an enlargement of the drain current changes at lower concentrations. The drain current changes were linearly proportional to the $CO_2$ concentration for all the tested temperatures. However, the HEMT sensors showed higher sensitivity for the higher testing temperatures. There was a noticeable change of the sensitivity from the sensors tested at 61° C. to those tested at 108° C. This difference is likely due to higher ambient temperature increasing the reaction rate between amine groups and $CO_2$ as well as the diffusion of $CO_2$ molecules into the PEI thin film. FIG. 5 shows the reversible and reproducible characteristics of PEI/starch functionalized HEMT sensors. The sensor was exposed to two different $CO_2$ concentrations twice at 28.5% and 37.5%, respectively. Similar responses were obtained for the same $CO_2$ concentration for both cases.

As provided by the foregoing examples, PEI/starch functionalized HEMT sensors for $CO_2$ detection can have a wide dynamic range, which was demonstrated in the examples from 0.9% to 50%. The sensors were operated at low bias voltage (0.5 V) for low power consumption applications. The sensors appear to provide higher sensitivity at temperatures higher than ~100° C. Accordingly, embodiments of the subject device can be integrated with a commercial available hand-held wireless transmitter to realize a portable, fast and high sensitive $CO_2$ sensor.

EXAMPLE $O_2$ Recognition Layer-gated Functionalized HEMT

The schematic cross-section of an oxygen sensor according to an embodiment of the present invention is shown in FIG. 6. The IZO-gated AlGaN/GaN HEMT structures used for the examples have a 3 μm thick undoped GaN buffer, a 30 Å thick $Al_{0.3}Ga_{0.7}N$ spacer, and a 220 Å thick Si-doped $Al_{0.3}Ga_{0.7}N$ cap layer. The epi-layers were grown by RF plasma-assisted Molecular Beam Epitaxy on the thick GaN buffers produced on sapphire substrates by metal organic chemical vapor deposition (MOCVD). Mesa isolation was performed by Inductively Coupled Plasma (ICP) etching with $Cl_2$/Ar based discharges at −90 V dc self-bias, ICP power of 300 W at 2 MHz and a process pressure of 5 mTorr. Ohmic contacts each having an area of 50×50 μm$^2$ and separated with gap of 50 µm were formed of e-beam deposited Ti/Al/Pt/Au patterned by lift-off. The contacts were annealed at 850° C. for 45 sec under flowing $N_2$.

The IZO film was deposited on the gate area by co-sputtering the ZnO and the $In_2O_3$ targets simultaneously and had a high carrier concentration of ~$10^{21}$ cm$^{-3}$. Specifically, a 60 Å-thick IZO film was deposited as the gate with a length of 40 µm and a width of 60 µm patterned by e-beam lithography. The IZO film was deposited near room temperature by radio frequency (RF) magnetron sputtering using 4 inch diameter targets of $In_2O_3$ and ZnO. The temperature at the substrate surface was 40 C after the a-IZO deposition, as determined from temperature indicators attached to reference glass substrates. The working pressure was 5 mTorr in pure Ar. The film has a carrier concentration of ~$10^{21}$ cm$^{-3}$ and electron mobility of 10~20 cm$^2$V$^{-1}$s$^{-1}$ obtained from Hall measurements. The sputtering power on the targets was held constant at 125 W, leading to compositions of the films measured by x-ray fluorescence spectroscopy of In/Zn=0.5 in atomic ratio. The typical thickness of the IZO films deposited was 150 nm, with a root mean square roughness of 0.4 nm measured over a 10×10 µm$^2$ area by Atomic Force Microscopy. The films were amorphous as determined by x-ray diffraction.

The effect of temperature and $O_2$ concentration on the sensing sensitivity was investigated using the above described devices.

The device was tested in a furnace tube, which allowed the pure or mixed oxygen and nitrogen flow into the tube. For these examples, the source-drain currents were measured using an Agilent 4156C parameter analyzer with the gate region exposed.

Figure 7:
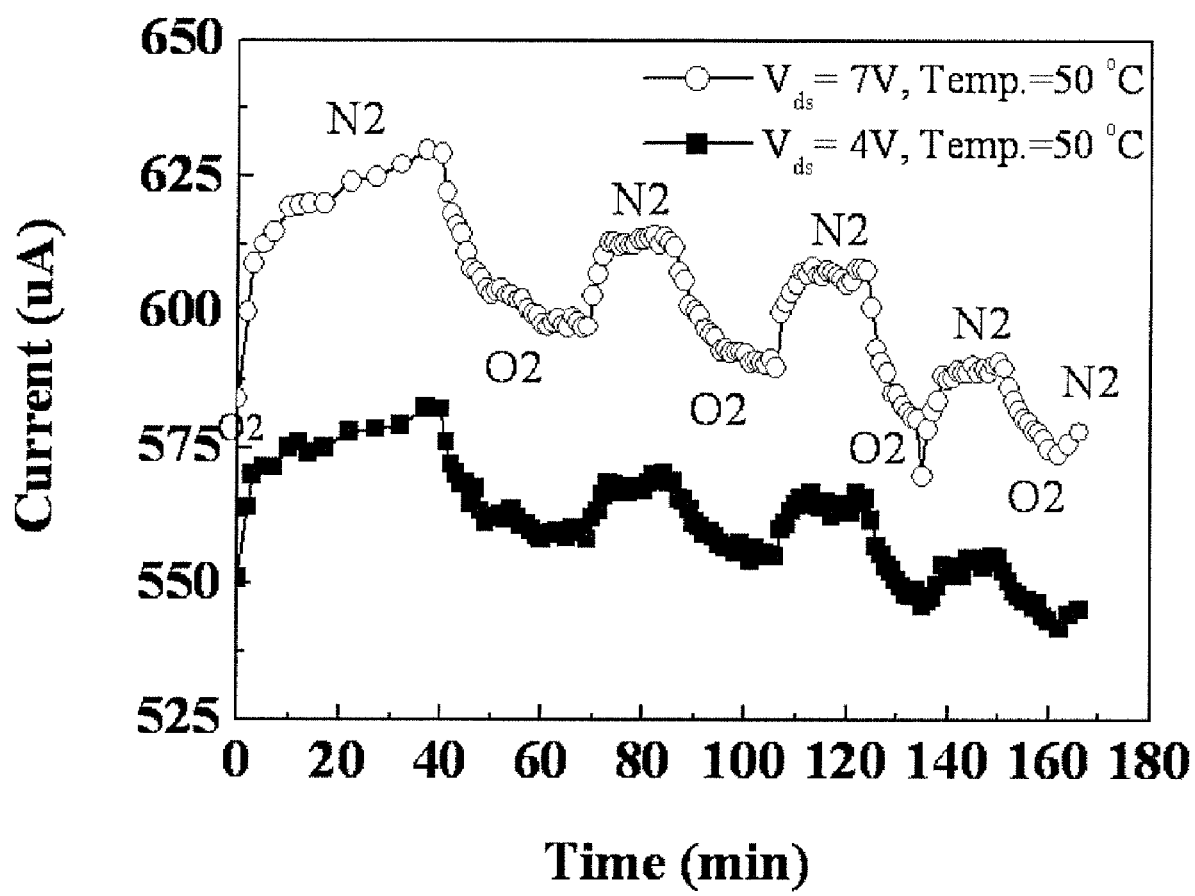
FIG. 7 shows a plot of $I_{ds}$ vs. time. The device was tested at 50° C. in pure nitrogen and pure oxygen alternatively at $V_{ds}$=4V and 7V, respectively.

FIG. 7 shows that the device had a strong response when it was tested at 50° C. alternating between pure nitrogen and pure oxygen. This device was tested at both $V_{ds}$=4V and $V_{ds}$=7V. When the device was exposed to the oxygen, the drain-source current decreased, and when the device was exposed to nitrogen, the current increased. The high response of this sensor was attributed to the high carrier concentration in the IZO film, that is, the high concentration of oxygen vacancy. The IZO film provides superior high oxygen vacancy concentration which enable this IZO film easily sense oxygen and create a potential on the gate area of the AlGaN/GaN HEMT. A sharp drain-source current change demonstrates the combination of the advantage of the high electron mobility of the HEMT and the high oxygen vacancy concentration of the IZO film. Because of these combined advantages, this oxygen sensor can operate with a high sensitivity at such a near room temperature (50° C.) compared to many related art oxide-based oxygen sensors, which operate from 400° C. to 700° C. At higher drain-source voltage ($V_{ds}$=7V), the device has a stronger response than the lower biased one. The response is usually observed at the AlGaN/GaN HEMT based sensor and can be attributed to the high field effect. Referring to FIG. 7, it can be seen that the baseline of the $I_{ds}$ is gradually decreasing after several $O_2/N_2$ cycles, this decreasing trend resulted from the decreasing number of oxygen vacancies because the thermal energy of the IZO film at 50° C. is not enough to drive all the oxygen coming from the environment out of the IZO film. This result means that the life time of the oxygen sensor is limited and at a certain time, the sensor will lose its sensitivity unless the IZO film is re-activated at a higher temperature.

Figure 8:
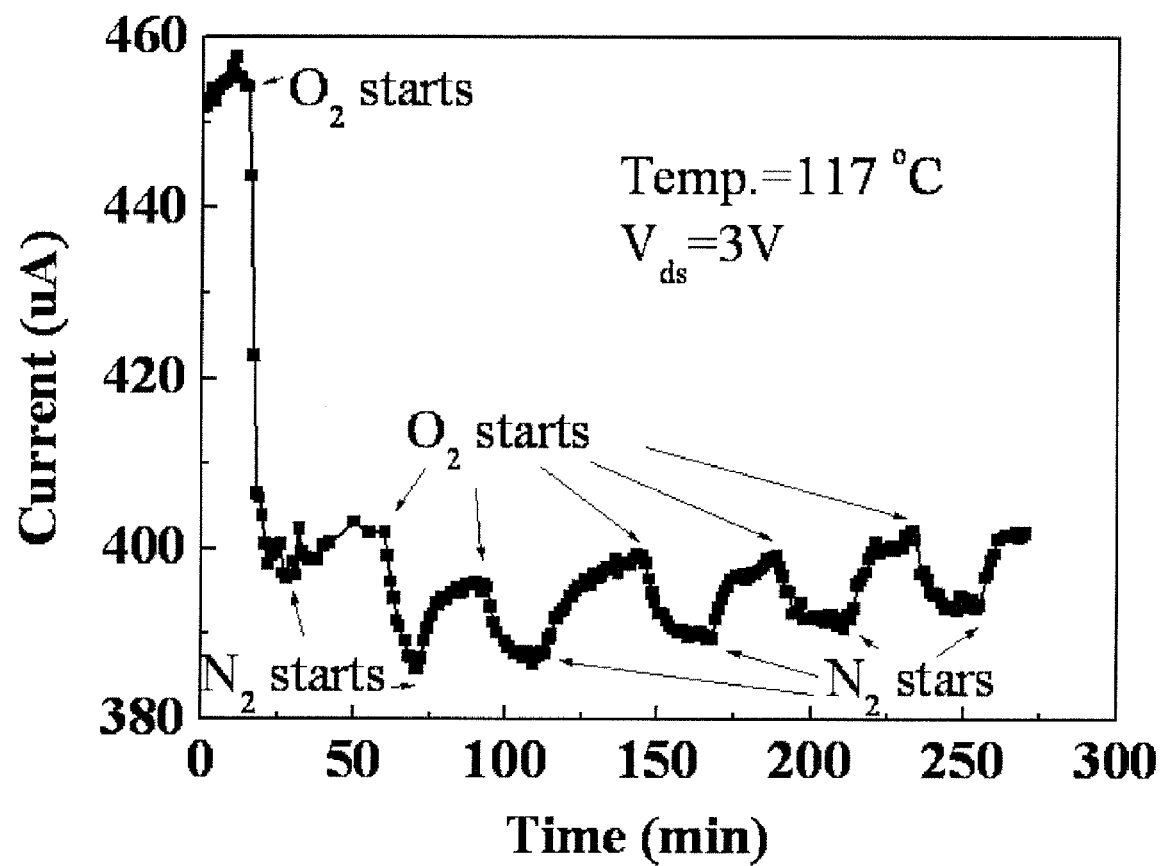
FIG. 8 shows a plot of $I_{ds}$ vs. time. The device was heated up to 360° C. in pure nitrogen and then cool down and tested at 117° C. in pure nitrogen and in pure oxygen alternatively at $V_{ds}$=3V.

FIG. 8 shows a plot for a device that was heated up to 360° C. in pure nitrogen in the beginning and then cooled down and tested at 117° C. alternating between pure nitrogen and pure oxygen at $V_{ds}$=3V. When the first time the oxygen was flowed into the tube, the device showed a very strong and sharp response in $I_{ds}$. This is due to the excess oxygen vacancies produced in the IZO film at higher temperature. The high temperature re-activated the device that was saturated in the oxygen test at 50° C. After two $O_2/N_2$ cycles, the device reached the thermal equilibrium, from the 3$^{rd}$ to the 6$^{th}$ $O_2/N_2$ cycle, the $I_{ds}$ changes uniformly and still has good response and the device does not show any saturation. It is explained that the thermal energy of the oxygen in the IZO film can get enough kinetic energy to get away from the IZO film and reach a steady-state with the oxygen vacancy. Compared with traditional oxide-based $O_2$ sensors, this operation temperature (117° C.) is still quite low. From FIG. 8, it appears that there are two options for using this IZO-gated AlGaN/GaN HEMT sensor. The first option is to use the device at steady-state such as the 3$^{rd}$ to the 6$^{th}$ $O_2/N_2$ cycle. The second option is to use the excess states, such as the first $O_2/N_2$ cycle. The reason to use the excess state is its high sensitivity.

Accordingly, for inexpensive sensors, the device can be made disposable for a single use. In one embodiment, only the first shot is used to test oxygen and then the sensor can be disposed or recycled. In an embodiment, the device can be recycled by annealing the device again at a higher temperature, such as for example, 360° C., to re-activate the IZO film.

Figure 9:
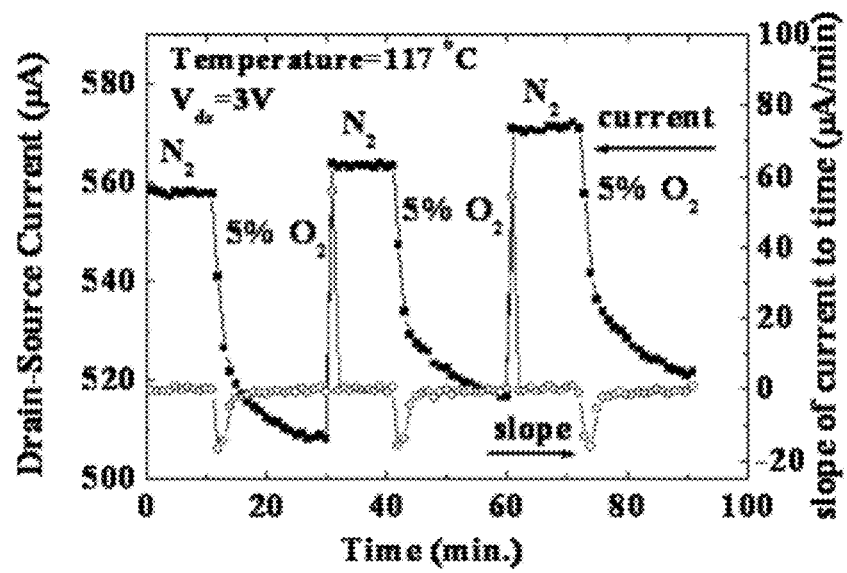
FIG. 9 shows a plot of $I_{ds}$ and the slope of $I_{ds}$ vs. time. The device was tested at 117° C. in nitrogen and 5% of $O_2/N_2$ alternatively. Three cycles of $N_2$ and 5% of $O_2/N_2$ were tested. After each cycle, the device was heated up to 360° C. and then cooled down to 117° C. for testing.

FIG. 9 shows the drain-source current and the slope of $I_{ds}$ vs. time of the device tested at 117° C. alternating between nitrogen and 5% of $O_2/N_2$. Three cycles of the alternating $N_2$ and 5% of $O_2/N_2$ were tested. After each cycle, the device was heated up to 360° C. and then cooled down to 117° C. for testing. Although the base-line of the $I_{ds}$ is increasing, the slope of the $I_{ds}$ vs. time remains the same for each cycle. This makes the sensor utilization much easier and simpler. Since the excess-state is very sensitive, the device was tested in an ambient with a 1.67% and a 200 ppm of $O_2/N_2$, respectively, at 117° C. and $V_{ds}$=7V. The slope of the $I_{ds}$ vs. time for the 1.67% and the 200 ppm of $O_2/N_2$ are 101 µA/min and 17 µA/min, respectively. The slopes show that the device still has a very strong response at very low $O_2$ concentration. The combined advantage of excess-state in IZO film, high electron mobility in AlGaN/GaN, and the high field effect make the low concentration $O_2$ testing very easy.

Indium zinc oxide (IZO)-gated AlGaN/GaN high electron mobility transistors (HEMTs) were used to detect oxygen gas. The IZO gated-AlGaN/GaN HEMT drain-source current ($I_{ds}$) showed a strong response to the oxygen gas at low temperatures of 50° C. and 117° C. This $O_2$ sensor shows a high sensitivity and wide detection limit ranging from 200 ppm to 100% of $O_2/N_2$ ratio. These results clearly demonstrate electronic biological sensors based on AlGaN/GaN HEMTs for $O_2$ detection.

In summary, a combination of IZO film and the AlGaN/GaN HEMT structure can detect oxygen from 200 ppm to 100% at low temperatures, such as 117° C. The sensor can be used in the steady-state or in the excess-state which provide flexibility in various applications. Embodiments of the subject device can realize a portable, fast response and high sensitivity oxygen detector.

Although embodiments have been described with reference to a number of illustrative embodiments thereof, it should be understood that numerous other modifications and embodiments can be devised by those skilled in the art that will fall within the spirit and scope of the principles of this disclosure. More particularly, various variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. A sensor, comprising:
   a high electron mobility transistor (HEMT) on a substrate; and
   a polymer-based solar cell connected to the HEMT.

2. The sensor according to claim 1, wherein an N-type region of the polymer based solar cell is connected to a source region of the HEMT.

3. The sensor according to claim 2, wherein the HEMT comprises a source electrode on the source region of the HEMT, wherein the N-type region of the polymer based solar cell is connected to the source region of the HEMT by a via through a dielectric layer on the source electrode of the HEMT.

4. The sensor according to claim 1, wherein the polymer based solar cell is provided on a gate region of the HEMT.

5. The sensor according to claim 4, wherein the polymer based solar cell comprises a P-type layer on the gate region of the HEMT and an N-type layer on the P-type layer.

6. The sensor according to claim 5, wherein the P-type layer directly contacts a surface layer of the HEMT at the gate region of the HEMT.

7. The sensor according to claim 5, wherein the N-type layer is electrically connected to a source region of the HEMT.

8. The sensor according to claim 1, wherein the sensor is connected in an IR detection system to measure $CO_2$ and/or oxygen.

9. The sensor according to claim 1, wherein carbon dioxide and/or oxygen concentration is determined by the intensity of light absorbed by the solar cell and amplified by the HEMT.

10. The sensor according to claim 9, further comprising nanoparticles or nanorods and dyes in the polymer of the polymer-based solar cell for tuning light absorption wavelengths of the polymer-based solar cell.

11. A method of detecting oxygen and carbon dioxide in exhaled breath, comprising:
    providing a sensor device in or near exhaled breath of a patient, wherein the sensor device comprises:
       a first high electron mobility transistor (HEMT) on a substrate and comprising a carbon dioxide selective recognition layer on a gate region of the first HEMT, the carbon dioxide selective recognition layer being a material that reacts with carbon dioxide to result in a change in charge to the carbon dioxide selective recognition layer upon exposure to carbon dioxide; and
       a second HEMT on the substrate and comprising an oxygen selective recognition layer on a gate region of the second HEMT, wherein the oxygen selective recognition layer has a high oxygen vacancy concentration;
    detecting carbon dioxide in the exhaled breath using the first HEMT; and
    detecting oxygen in the exhaled breath using the second HEMT.

12. The method according to claim 11, further comprising:
    recycling the second HEMT by performing an annealing process; and
    performing a second test of the oxygen and carbon dioxide in the exhaled breath using the sensor device.

13. A method of detecting oxygen and carbon dioxide in exhaled breath, comprising:
    providing an infrared (IR) detection system in or near a path of exhaled breath of a patient, wherein the IR detection system comprises:
       a polymer based solar cell on a gate region of a high electron mobility transistor (HEMT), wherein the polymer based solar cell converts incident light into electric signals and the HEMT amplifies the electric signals; and
    detecting oxygen and/or carbon dioxide in the exhaled breath according to the incident light absorbed by the polymer based solar cell.

14. The method according to claim 13, wherein the polymer based solar cell comprises a P-type layer on the gate region of the HEMT and an N-type layer on the P-type layer.

15. The method according to claim 14, wherein the P-type layer directly contacts a surface layer of the HEMI at the gate region of the HEMT.

16. The method according to claim 14, wherein the N-type layer is electrically connected to a source region of the HEMT.

17. The method according to claim 13, wherein the IR detection system further comprises a light source configured to provide incident light onto the polymer based solar cell, wherein the light passes through the exhaled breath of the patient.

18. The method according to claim 17, wherein carbon dioxide and/or oxygen concentration is determined by the intensity of the light passing through the exhaled breath of the patient and absorbed by the solar cell.

19. A method of detecting oxygen and carbon dioxide in exhaled breath, comprising:
    providing an infrared (IR) detection system in or near a path of exhaled breath of a patient, wherein the IR detection system comprises:
       a high electron mobility transistor (HEMT); and
       a polymer based solar cell connected to the HEMT,
          wherein the polymer based solar cell converts incident light into electric signals and the HEMT amplifies the electric signals; and
    detecting oxygen and/or carbon dioxide in the exhaled breath according to the incident light absorbed by the polymer based solar cell.

20. The method according to claim 19, wherein the JR detection system further comprises a light source configured to provide incident light onto the polymer based solar cell, wherein the light passes through the exhaled breath of the patient.

21. The method according to claim 20, wherein carbon dioxide and/or oxygen concentration is determined by the intensity of the light passing through the exhaled breath of the patient and absorbed by the solar cell.

22. A method of detecting oxygen in exhaled breath, the method comprising:
    providing an oxygen sensor in or near exhaled breath of a patient, wherein the oxygen sensor comprises a high electron mobility transistor (HEMT) comprising a selective recognition layer on a gate region, wherein the selective recognition layer has a high oxygen vacancy concentration;
    detecting oxygen in the exhaled breath using the oxygen sensor; and
    recycling the oxygen sensor for additional testing by performing an annealing process.

23. The method according to claim 22, wherein the oxygen sensor is disposable.

* * * * *

UNITED STATES PATENT AND TRADEMARK OFFICE
CERTIFICATE OF CORRECTION

PATENT NO. : 8,222,041 B2  
APPLICATION NO. : 12/990377  
DATED : July 17, 2012  
INVENTOR(S) : Fan Ren and Stephen John Pearton It is certified that error appears in the above-identified patent and that said Letters Patent is hereby corrected as shown below:

Abstract,  
Line 2, "disclosed, hi one" should read --disclosed. In one--.

Column 12,  
Line 14, "layer of the HEMI" should read --layer of the HEMT--.  
Line 42, "wherein the JR" should read --wherein the IR--.

Signed and Sealed this  
Ninth Day of October, 2012

David J. Kappos  
*Director of the United States Patent and Trademark Office*